US00PP37200P3

(12) United States Plant Patent
Schoone

(10) Patent No.: US PP37,200 P3
(45) Date of Patent: Jan. 6, 2026

(54) ***PHALAENOPSIS* PLANT NAMED 'Tailwind'**

(50) Latin Name: *Phalaenopsis hybrida*
Varietal Denomination: Tailwind

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/975,980

(22) Filed: Dec. 10, 2024

(65) Prior Publication Data

US 2025/0194447 P1 Jun. 12, 2025

Related U.S. Application Data

(60) Provisional application No. 63/608,785, filed on Dec. 11, 2023.

(51) Int. Cl.
*A01H 5/02* (2018.01)
*A01H 5/12* (2018.01)
*A01H 6/62* (2018.01)

(52) U.S. Cl.
USPC ..... Plt./311
CPC ..... *A01H 6/62* (2018.05); *A01H 5/02* (2013.01); *A01H 5/12* (2013.01)

(58) Field of Classification Search
USPC ..... Plt./311
See application file for complete search history.

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'Tailwind', characterized by its upright plant habit; upright flowering stems; freely flowering habit with typically two inflorescences developing per plant, each inflorescence with numerous flowers; and white-colored flowers with white and yellow-colored labella.

2 Drawing Sheets

Figure 1:
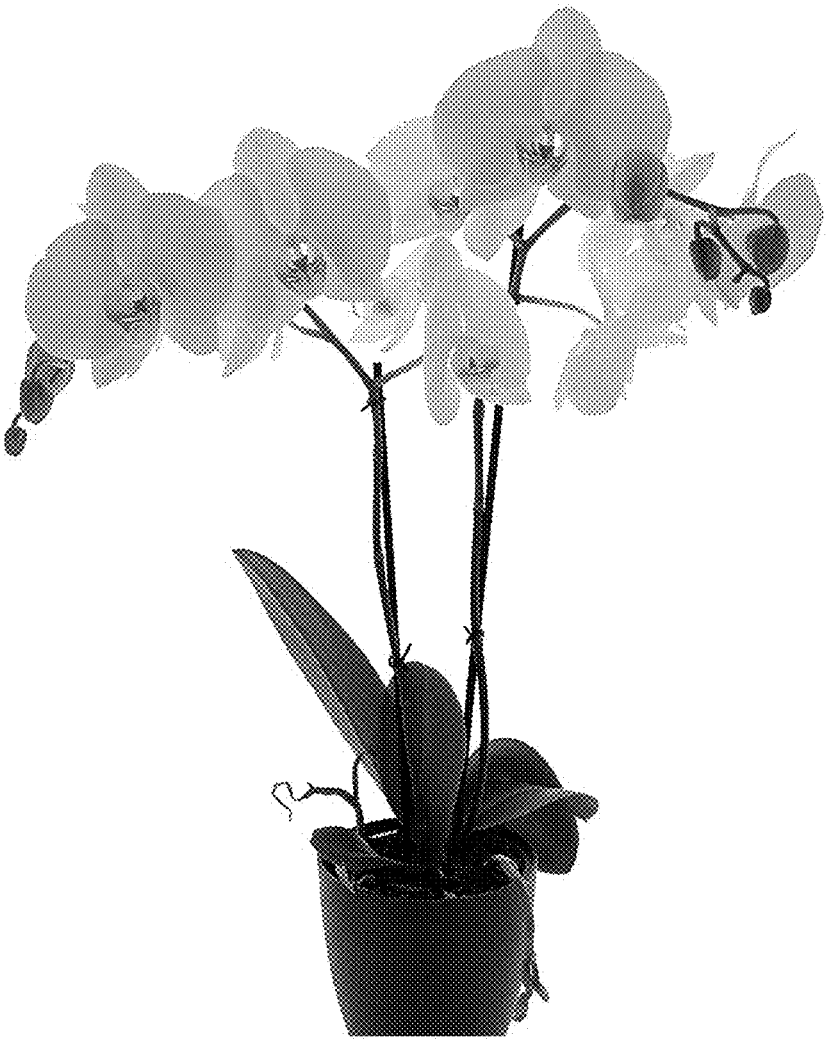

Botanical designation: *Phalaenopsis hybrida.*
Cultivar denomination: 'TAILWIND'.

CROSS-REFERENCED TO CLOSELY-RELATED APPLICATIONS

Title: Varieties of *Phalaenopsis* Plants
Inventor: René Schoone
Filed: Dec. 11, 2023
Ser. No. 63/608,785

Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Dec. 2, 2023, application number 2023/2629. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Tailwind'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with unique flower patterns and coloration.

The new *Phalaenopsis* plant originated from a cross-pollination in December 2014 in Assendelft, The Netherlands of *Phalaenopsis hybrida* 'Silver Light', disclosed in U.S. Plant Pat. No. 24,387, as the female, or seed, parent with a proprietary selection of *Phalaenopsis hybrida* identified as code number ZT817, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November 2019.

Asexual reproduction of the new *Phalaenopsis* plant by in vitro meristem propagation in a controlled environment in Assendelft, The Netherlands since November 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Tailwind'. These characteristics in combination distinguish 'Tailwind' as a new and distinct *Phalaenopsis* plant:

1. Upright plant habit.
2. Upright flowering stems.
3. Freely flowering habit with typically two inflorescences developing per plant, each inflorescence with numerous flowers.

4. White-colored flowers with white and yellow-colored labella.

Plants of the new *Phalaenopsis* can be compared to plants of the female parent, 'Silver Light'. Plants of the new *Phalaenopsis* differ primarily from plants of 'Silver Light' in leaf length as plants of the new *Phalaenopsis* have longer leaves than plants of 'Silver Light'. In addition, plants of the new *Phalaenopsis* have more flowers per inflorescence than plants of 'Silver Light'.

Plants of the new *Phalaenopsis* can be compared to plants of the male parent selection. Plants of the new *Phalaenopsis* differ primarily from plants of the male parent selection in flower diameter as plants of the new *Phalaenopsis* have broader flowers than plants of the male parent selection. In addition, leaves of plants of the new *Phalaenopsis* are not as erect as leaves of plants of the male parent selection.

Plants of the new *Phalaenopsis* can be compared to plants of *Phalaenopsis hybrida* 'Road Trip', not patented. In side-by-side comparisons, plants of the new *Phalaenopsis* differ primarily from plants of 'Road Trip' in labella color as flowers of plants of the new *Phalaenopsis* have white and yellow-colored labella whereas flowers of plants of 'Road Trip' have mostly white and light orange-colored labella. In addition, petals of plants of the new *Phalaenopsis* are more separate ("free") from each other than petals of plants of 'Road Trip' which are somewhat imbricate.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Tailwind' grown in a container.

Figure 2:
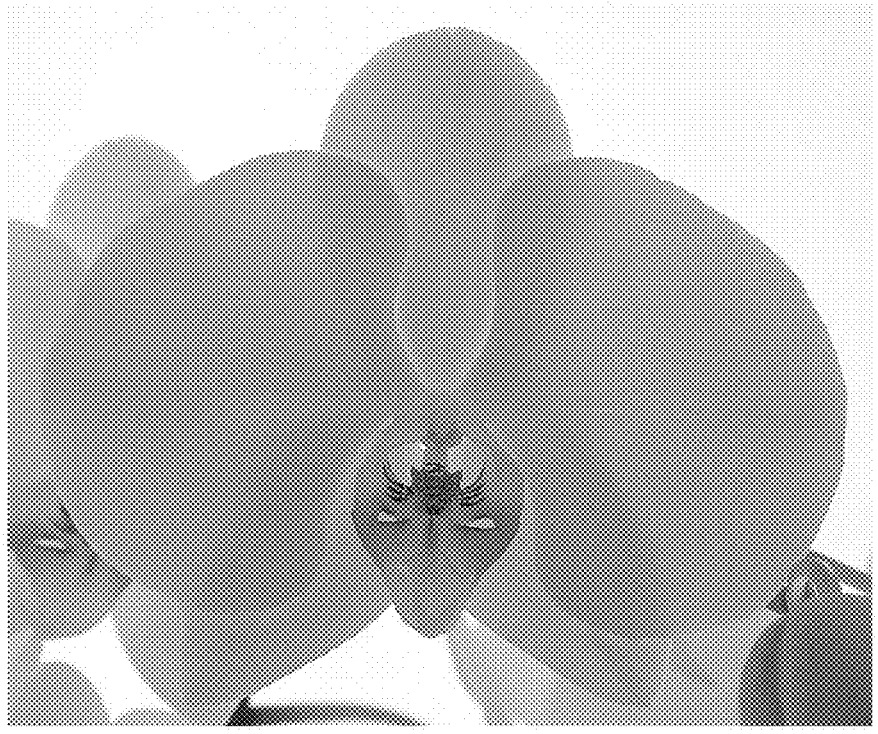

The photograph on the second sheet (FIG. 2) is a close-up view of a typical flower of 'Tailwind'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Tailwind'.

Parentage:

*Female, or seed, parent.*—*Phalaenopsis hybrida* 'Silver Light', disclosed in U.S. Plant Pat. No. 24,387.

*Male, or pollen, parent.*—Proprietary selection of *Phalaenopsis hybrida* identified as code number ZT817, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial.

*Plant height, substrate level to top of foliar plane.*—About 13.9 cm.

*Plant height, substrate level to top of floral plane.*—About 42.8 cm.

*Plant diameter or spread.*—About 36.3 cm.

Leaf description:

*Arrangement and quantity.*—Distichous, simple; sessile; about four to six fully-developed leaves per plant.

*Length.*—About 20.7 cm.

*Width.*—About 7.6 cm.

*Aspect.*—Horizontal to somewhat erect.

*Shape.*—Broadly elliptic to elliptic-oblong or elliptic-obovate; slightly to moderately carinate.

*Apex.*—Unequal broadly acute to unequal obtuse.

*Base.*—Sheathing. Sheath length: About 1.4 cm. Sheath width: About 1.2 cm. Sheath color, upper and lower surfaces: Close to 144A; towards the margins, close to 143B.

*Margin.*—Entire.

*Texture and luster, upper surface.*—Smooth, glabrous; slightly to moderately glossy.

*Texture and luster, lower surface.*—Smooth, glabrous; moderately glossy.

*Venation pattern.*—Camptodromous.

*Color.*—Developing leaves, upper surface: Close to 147A; narrow marginal edges, close to 144C. Developing leaves, lower surface: Close to 146B; towards the margins, close to NN137B with narrow marginal edges, close to 138C. Fully expanded leaves, upper surface: Close to NN137B; narrow marginal edges, close to 143B; venation, close to NN137A. Fully expanded leaves, lower surface: Close to 146B; towards the margins, close to 146A; venation, close to 143A.

Inflorescence description:

*Appearance and flowering habit.*—Showy zygomorphic flowers arranged on axillary simple or branched racemes; typically two inflorescences develop per plant; each inflorescence with about ten flowers; flowers face outwardly on outwardly arching inflorescences supported by upright peduncles; flowers with three petals, two lateral petals and one center petal transformed into a labellum and three sepals.

*Fragrance.*—None detected.

*Time to flower*.—Plants begin flowering about five months after planting; plants flower naturally during the winter into the spring.

*Flower longevity and postproduction longevity*.—Long flowering period and long shelf life, individual flowers last for about seven weeks on the plant; flowers not persistent.

*Inflorescence length* (*lowermost flower to inflorescence apex*).—About 32.6 cm.

*Inflorescence width*.—About 21.2 cm.

*Flower buds*.—Height: About 1.8 cm. Diameter: About 1.2 cm by 1.5 cm. Shape: Broadly ovate. Color: Close to 145A; towards the base, close to 144A and 144B.

*Flower size*.—About 10.3 cm (vertical) by 11.6 cm (horizontal).

*Flower depth*.—About 3.3 cm.

*Petals, quantity and arrangement*.—Three, two lateral petals and one center petal transformed into a labellum.

*Lateral petals*.—Length: About 5.6 cm. Width: About 7.2 cm. Shape: Broadly reniform to broadly lunate. Apex: Broadly obtuse. Margin: Entire. Texture and luster, upper and lower surfaces: Smooth, glabrous; moderately velvety; matte. Color: When opening, upper surface: Close to NN155D. When opening, lower surface: Close to 155C; towards the margins and apex, closer to NN155C. Fully opened, upper and lower surfaces: Close to NN155D.

*Labella*.—Appearance: Three-parted with two lateral lobes and a central lobe. Length, lateral lobes: About 2.5 cm. Width, lateral lobes: About 2 cm. Length, central lobe: About 2.7 cm. Width, central lobe: About 0.7 cm to 3.2 cm. Length, cirrhose apices: About 2.6 cm. Shape, lateral lobes: Obovate to close to spatulate. Shape, central lobe: Narrowly deltoid with an elongated apex. Apex, lateral lobes: Obtuse. Apex, central lobe: Emarginate with a minute acute apex and with two cirrhose apices curled backwards and slightly upright. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 7 mm in width and about 7 mm in height. Color, lateral lobes: When opening, upper surface: Close to NN155D; lower margins, close to 2A; at the base, axial stripes, close to 185C. When opening, lower surface: Close to NN155D; lower margins, close to 2A. Fully opened, upper surface: Close to NN155D; lower margins, close to 12A; at the base, axial stripes, close to 184A. Fully opened, lower surface: Close to NN155D; lower margins, close to 7A. Color, central lobe: When opening, upper surface: Close to NN155D; towards the base, close to 1A and 1B and at the base, close to NN155B with radial stripes, close to 187D; upper margin, tinged with close to 166B; midvein, tinged with close to 166B; cirrhose apices, close to NN155D and distally, close to 3C. When opening, lower surface: Close to NN155D; towards the base, close to 155C and 5A; marginal edges, close to 166B; cirrhose apices, close to NN155D and distally, close to 3C. Fully opened, upper surface: Close to NN155D; towards the base, close to 12B and at the base, close to NN155B with radial stripes, close to 187D; upper margin, tinged with close to 172A; midvein, tinged with close to 172A; cirrhose apices, close to NN155D and distally, close to 8C. Fully opened, lower surface: Close to NN155D; towards the base, close to 155C and 7A; marginal edges, close to 172A; cirrhose apices, close to NN155D and distally, close to 8C. Color, callosities: When developing: Close to 155A; towards the apex, close to 11D; towards the base, close to 13A with fine dots, close to 179A. Fully developed: Close to 155A; towards the apex, close to 11D; towards the base, close to 12A with fine dots, close to 179A.

*Sepals*.—Quantity and arrangement: Three, one upper dorsal sepal and two lower lateral sepals. Length, dorsal sepal: About 5.6 cm. Width, dorsal sepal: About 3.8 cm. Length, lateral sepals: About 5.7 cm. Width, lateral sepals: About 3.3 cm. Shape, dorsal sepal: Obovate. Shape, lateral sepals: Ovate. Apex, dorsal sepal: Broadly acute. Apex, lateral sepals: Acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 157C; towards the margins and apex, close to 155C. When opening, lower surface: Close to 145C; towards the margins, close to 157D. Fully opened, upper surface: Close to NN155B; towards the margins and apex, close to NN155D. Fully opened, lower surface: Close to 157C and 157D; towards the margins and apex, close to N155D. Color, lateral sepals: When opening, upper surface: Close to 157C; towards the base, close to a blend of 145C and 145D and at the base, sparse fine dots, close to 182D. When opening, lower surface: Close to 150C; towards the margins, close to 155D; midvein, close to 150A and 150B. Fully opened, upper surface: Close to 157C and 157D; towards the margins and apex, close to NN155D; at the base, sparse fine dots, close to 186C. Fully opened, lower surface: Close to a blend of 145D and 150D; towards the margins, close to NN155C and NN155D; midvein, close to 150C.

*Peduncles*.—Length: About 52.5 cm. Diameter: About 5 mm. Aspect: Upright to outwardly arching. Texture and luster: Smooth, glabrous; matte. Color: Close to 138A moderately to densely covered with fine dots, close to 144C.

*Pedicels*.—Length: About 5.4 cm. Diameter: About 3 mm. Aspect: About 60° from peduncle axis. Texture and luster: Smooth, glabrous; matte. Color: Close to 144C; distal end, close to 150D; proximal end, close to 144A.

*Reproductive organs*.—Androecium: Column length: About 9 mm. Column width: About 6 mm. Column color: Close to NN155D. Pollinia quantity: Two. Pollinia diameter (per two pollinia): About 3 mm. Pollinia color: Close to 21A. Gynoecium: Stigma length: About 3 mm. Stigma width: About 5 mm. Stigma shape: Reniform. Stigma color: Close to NN155D. Ovary length: About 8 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Tailwind' as herein illustrated and described.

* * * * *